US00PP31549P2

(12) United States Plant Patent
Stoppel

(10) Patent No.: US PP31,549 P2
(45) Date of Patent: Mar. 17, 2020

(54) CHERRY TREE NAMED 'PRIM 31'

(50) Latin Name: ***Prunus avium* L.**
Varietal Denomination: Prim 31

(71) Applicant: Peter Stoppel, Kressbronn (DE)

(72) Inventor: Peter Stoppel, Kressbronn (DE)

(73) Assignee: Cerasina GmbH, Kressbronn (DE)

( * ) Notice: Subject to any disclaimer, the term of this patent is extended or adjusted under 35 U.S.C. 154(b) by 0 days.

(21) Appl. No.: 16/501,498

(22) Filed: Apr. 18, 2019

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
CPC ..... A01H 5/08; A01H 6/74
See application file for complete search history.

*Primary Examiner* — Annette H Para
(74) *Attorney, Agent, or Firm* — The Webb Law Firm

(57) ABSTRACT

A new and distinct variety of sweet cherry tree that produces rounded and vivid red colored fruits with medium firm fruit flesh.

2 Drawing Sheets

Botanical classification: *Prunus avium* L.
Varietal denomination: 'Prim 31'.

BACKGROUND OF THE INVENTION

The present invention comprises a new and distinct variety of sweet cherry tree, botanically known as *Prunus avium* L., and referred to by the varietal name 'Prim 31'. The new variety was discovered in Baden-Wuerttemberg, Germany as the result of planned breeding between cherry tree variety named 'Sweet Early' (female parent, unknown patent protection) and an unnamed and unpatented cherry tree variety as the male parent. The purpose of the breeding program was to produce high quality fruits with an early ripening time. The new variety was first asexually reproduced via cuttings in Baden-Wuerttemberg, Germany in 2006. The new variety has been trial and field tested and has been found to retain its distinctive characteristics and remain true to type through successive propagations. The present invention has not been evaluated under all possible environmental conditions. The phenotype may vary with variations in environment without a change in the genotype of the plant.

The new variety is similar to both parental varieties in exhibiting a medium early blooming time, but differs from its parental varieties in fruit ripening time, fruit firmness, and S-alleles. When compared to cherry tree variety named 'PC 7144-7', known and marketed as "Tieton" (U.S. Plant Pat. No. 8,051), 'Prim 31' has S-alleles/S1S4 and "Tieton" has S-alleles/S3S9, the fruit shape of 'Prim 31' is rounder than the fruit of "Tieton", 'Prim 31' has a black-red fruit color and "Tieton" has a brown-black fruit color, 'Prim 31' exhibits a medium strong and wide tree habit versus the upright and strong tree habit of "Tieton", 'Prim 31' has a fruit ripening time that is 5 days earlier than "Tieton", and 'Prim 31' exhibits longer fruit stems and less fruit cracking than "Tieton". When compared to cherry tree variety named 'Prim 21' (plant patent application Ser. No. 16/501,496), the varieties are similar in flowering time and fruit color, but the fruits of 'Prim 31' ripen later and are bigger than the fruits of 'Prim 21'. Further, 'Prim 31' has S-alleles/S1S4 and 'Prim 21' has S-alleles/S3S9.

DESCRIPTION OF THE DRAWINGS

The accompanying photographic drawings illustrate the new variety at approximately 7 years of age with the color being as nearly true as is possible with color illustrations of this type.

DETAILED BOTANICAL DESCRIPTION

Figure 1:
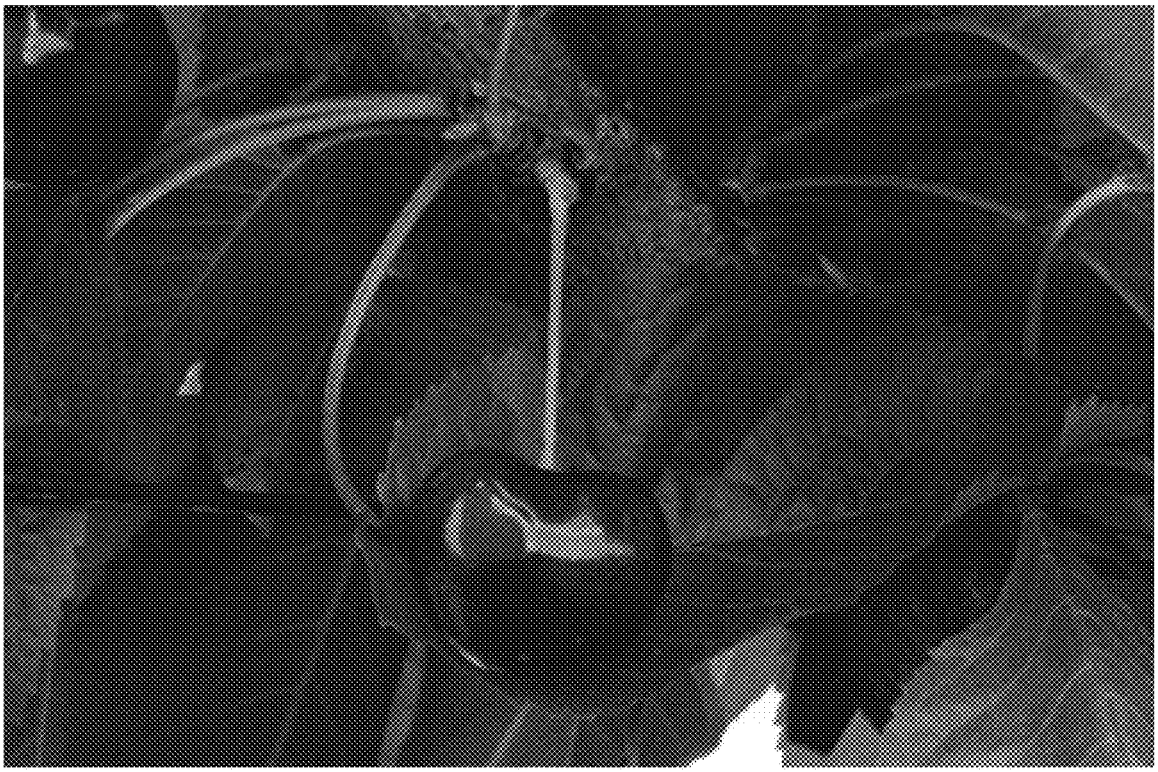
FIG. 1 is a close-up photograph of the fruit of 'Prim 31'.
Figure 2:
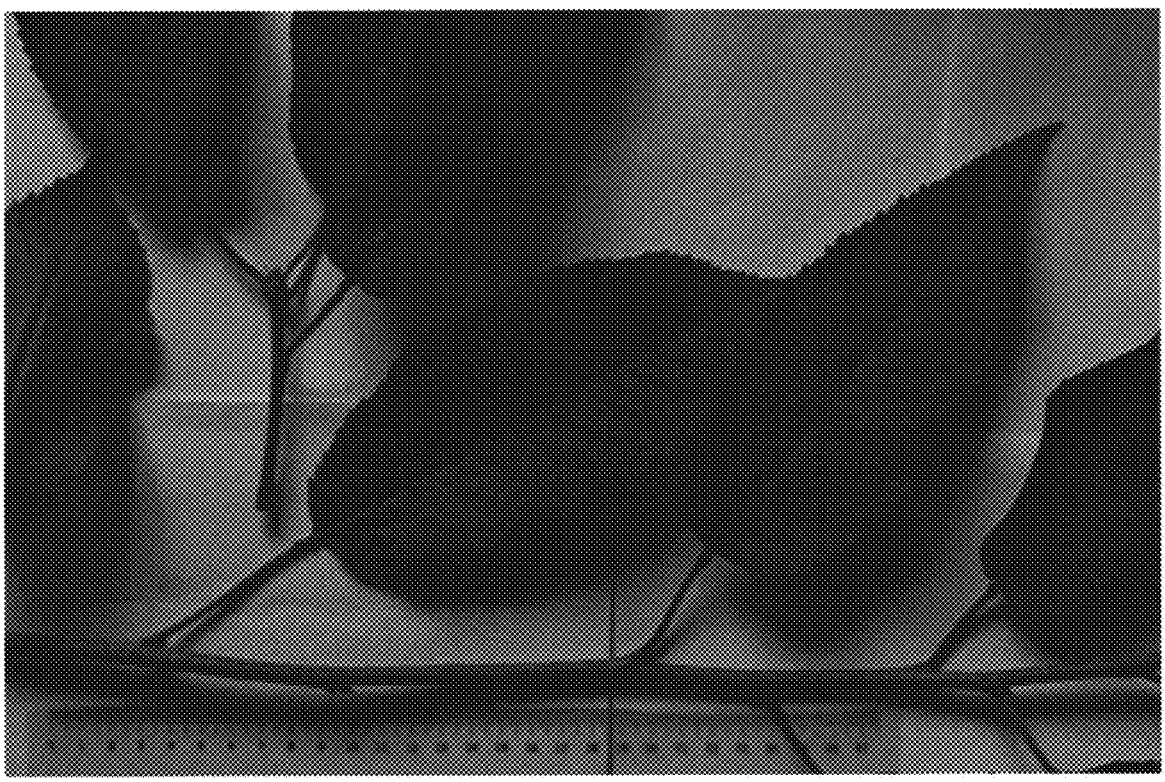
FIG. 2 is a close-up photograph of the leaves of 'Prim 31'.

The following detailed description sets forth the characteristics of the new variety. The data which defines these characteristics were collected by asexual reproductions via cuttings carried out in Kressbronn, Germany. The new variety was grown outside under natural soil conditions. The color readings were taken outside in natural daylight and the variety was approximately 7 years old when described. Color references are primarily to The R.H.S. Colour Chart of The Royal Horticultural Society of London, except where terms of ordinary significance are used.

TREE

Height: 3.0 m.
Width: 2.0 m, measured at 10.0 cm above ground level.
Vigor: Medium.
Density: Medium.
Form: Upright spread with a medium level of lateral branching.
Growth type: Spreading.
Bearing: Annually on spurs, with 3-4 bud positions located at the base of one-year old shoots.
Disease/pest resistance or susceptibility: Nothing unusual noted to date.

Trunk:

*Size*.—Medium.

*Bark color*.—RHS 199A.

*Surface texture*.—Smooth, with prominent lenticels.

*Lenticels*.—Length: 1.0-2.0 cm. Width: 0.5 cm. Density: Medium. Color: RHS 167A.

Branches:

*Diameter*.—0.5-1.5 cm.

*Surface texture*.—Of a typical sweet cherry tree; Smooth, with lenticels present.

*Color*.—RHS 164A.

*Form*.—Of a typical sweet cherry tree.

*Average angle*.—60-75 degrees.

*Bud arrangement*.—Of a typical sweet cherry tree.

*Lenticels*.—Length: About 1.0 mm. Width: About 1.0 mm. Shape: Rounded. Density: Few and scattered. Color: RHS 161B.

Leaves:

*Length*.—14.0-20.0 cm.

*Width*.—8.0-10.0 cm.

*Form*.—Long and narrow.

*Shape*.—Lanceolate.

*Texture*.—Leathery, no crisp feeling.

*Thickness*.—Medium.

*Apex*.—Acute.

*Base*.—Rounded.

*Margin*.—Irregularly serrate.

*Color*.—Upper surface: RHS 143A. Lower surface: RHS 142D.

*Petiole*.—Shape: Narrow. Length: 3.0-4.0 cm. Diameter: About 2.0 mm. Color: Adaxial surface: RHS 59A. Abaxial surface: RHS 149C. Venation: Type: Pinnate. Color: RHS 154D.

FLOWERS

Flower buds:

*Color*.—Reddish.

*Length*.—About 1.0 cm.

*Width*.—Under 1.0 cm.

*Pedicel*.—Length: 12.0 mm. Diameter: 0.4 mm.

Flowers:

*Bloom timing*.—Toward the end of April in Kressbronn, Germany.

*Blooming period*.—Medium to early in the season, similar to 'Burlat' (unpatented).

*Number of flowers per raceme*.—3 to 7.

*Pollination requirements*.—Cross-pollination needed.

*Petals*.—Number: 5 to 6. Length: 18.0 mm. Width: 18.0 mm. Shape: Round. Apex: Slightly obcordate. Margin: Slightly undulate. Texture: Soft. Color: RHS 155D (both surfaces).

*Sepals*.—Length: 5.0-7.0 mm. Width: About 5.0 mm. Shape: Conical. Margin: Regular. Color: RHS 143C (both surfaces).

Reproductive organs:

*Stamens*.—Number per flower: 4 to 5. Filament: Length: 12.0 mm. Width: 0.1 mm.

*Anthers*.—Shape: Kidney. Length: 0.6 mm. Color: RHS 13B.

*Pollen*.—Color: RHS 13B. Amount: Plentiful.

*Pistil length*.—12.0 mm.

*Style*.—Length: 4.0-6.0 mm. Color: RHS 143C.

*Stigma*.—Shape: Oval. Color: Green.

FRUIT

Fruit:

*Maturity when described*.—Eating maturity.

*Size*.—Diameter: 2.8-3.0 cm. Length: 3.4 cm.

*Skin*.—Thickness: Medium. Texture: Medium. Tendency to crack: Not prone to cracking from rain. Color: RHS 46A.

*Flesh*.—Aroma: Pleasant. Color: RHS 46B. Texture: Medium firm. Eating quality: Good.

*Seeds*.—Number per fruit: 1. Length: 1.3 cm. Breadth: 0.6-0.8 cm. Form: Oval. Color: Light brown.

*Stem*.—Length: 4.5 cm. Width: 0.2 cm. Color: Light green.

I claim:

1. A new and distinct variety of cherry tree, as is herein illustrated and described.

* * * * *